US011352462B2

(12) United States Patent
Nefzger et al.

(10) Patent No.: US 11,352,462 B2
(45) Date of Patent: Jun. 7, 2022

(54) FLAME-RETARDED RIGID POLYURETHANE FOAMS

(71) Applicant: Covestro Deutschland AG, Leverkusen (DE)

(72) Inventors: Hartmut Nefzger, Pulheim (DE); Persefoni Hilken, Cologne (DE); Markus Meuresch, Cologne (DE); Aurel Wolf, Wülfrath (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 57 days.

(21) Appl. No.: 16/764,211

(22) PCT Filed: Dec. 12, 2018

(86) PCT No.: PCT/EP2018/084509
§ 371 (c)(1),
(2) Date: May 14, 2020

(87) PCT Pub. No.: WO2019/121215
PCT Pub. Date: Jun. 27, 2019

(65) Prior Publication Data

US 2020/0392276 A1 Dec. 17, 2020

(30) Foreign Application Priority Data

Dec. 18, 2017 (EP) .................................... 17207933

(51) Int. Cl.

| | |
|---|---|
| ***C08G 18/38*** | (2006.01) |
| ***C08G 18/40*** | (2006.01) |
| ***C08G 18/42*** | (2006.01) |
| ***C08G 18/50*** | (2006.01) |
| ***C08G 18/66*** | (2006.01) |
| ***C08J 9/00*** | (2006.01) |
| ***C08J 9/14*** | (2006.01) |

(52) U.S. Cl.
CPC ..... *C08G 18/3831* (2013.01); *C08G 18/4018* (2013.01); *C08G 18/4202* (2013.01); *C08G 18/4213* (2013.01); *C08G 18/4238* (2013.01); *C08G 18/5024* (2013.01); *C08G 18/6696* (2013.01); *C08J 9/0038* (2013.01); *C08J 9/141* (2013.01); *C08G 2110/005* (2021.01); *C08G 2110/0025* (2021.01); *C08G 2110/0058* (2021.01); *C08G 2110/0066* (2021.01); *C08J 2203/14* (2013.01); *C08J 2205/10* (2013.01); *C08J 2375/12* (2013.01)

(58) Field of Classification Search
CPC .. B32B 5/18; B32B 5/20; B32B 5/245; B32B 15/046; B32B 15/12; B32B 15/20; B32B 19/047; B32B 21/02; B32B 21/047; B32B 29/007; B32B 29/02; B32B 2266/0278; B32B 2307/102; B32B 2307/3065; B32B 2307/72; B32B 2419/00; C07C 269/04; C07C 271/20; C08G 18/092; C08G 18/1816; C08G 18/225; C08G 18/3831; C08G 18/4018; C08G 18/4202; C08G 18/4211; C08G 18/4213; C08G 18/4238; C08G 18/425; C08G 18/5021; C08G 18/5024; C08G 18/66; C08G 18/6696; C08G 18/7664; C08G 2110/0025; C08G 2110/005; C08G 2110/0058; C08G 2110/0066; C08J 9/0014; C08J 9/0019; C08J 9/0023; C08J 9/0038; C08J 9/0061; C08J 9/141; C08J 2201/022; C08J 2203/14; C08J 2205/052; C08J 2205/10; C08J 2375/04; C08J 2375/12; C08J 2483/12; C08K 5/521
See application file for complete search history.

(56) References Cited

U.S. PATENT DOCUMENTS

| | | | | |
|---|---|---|---|---|
| 4,120,834 | A | 10/1978 | Fatutto | |
| 4,987,156 | A * | 1/1991 | Tozune | C08G 18/2063 521/99 |
| 5,585,413 | A * | 12/1996 | Nagashima | C08G 18/76 521/159 |
| 8,097,741 | B2 | 1/2012 | Webster et al. | |
| 2006/0160979 | A1 | 7/2006 | Benecke | |

(Continued)

FOREIGN PATENT DOCUMENTS

| | | | |
|---|---|---|---|
| EP | 1548001 | A1 | 6/2005 |
| EP | 1571167 | A2 | 9/2005 |
| EP | 3098251 | A1 | 11/2016 |

(Continued)

OTHER PUBLICATIONS

International Search Report for International Patent Application No. PCT/EP2018/084509, dated Mar. 4, 2019.

(Continued)

*Primary Examiner* — John M Cooney
(74) *Attorney, Agent, or Firm* — K&L Gates LLP

(57) ABSTRACT

A process for producing rigid PUR/PIR foams comprising A1 an isocyanate-reactive component, A2 a flame retardant, A3 a blowing agent, A4 a catalyst, A5 optionally auxiliaries and additives, and B an organic polyisocyanate component. Component A1 comprises a triurethane triol A1.1 and a compound A1.2 selected from the group consisting of polyether polyol, polyester polyol, polyether carbonate polyol, and polyether ester polyol. Also disclosed is a rigid PUR/PIR foam, an insulating material, a composite element, and a mixture.

10 Claims, No Drawings

(56) References Cited

U.S. PATENT DOCUMENTS

| | | | | |
|---|---|---|---|---|
| 2010/0210748 | A1* | 8/2010 | Leimenstoll | C09J 175/08 521/159 |
| 2014/0288198 | A1* | 9/2014 | Awahara | C08J 9/30 521/56 |

FOREIGN PATENT DOCUMENTS

| | | | |
|---|---|---|---|
| WO | 03066580 | A1 | 8/2003 |
| WO | 2015138684 | A2 | 9/2015 |

OTHER PUBLICATIONS

Written Opinion for International Patent Application No. PCT/EP2018/084509, dated Mar. 4, 2019.

* cited by examiner

FLAME-RETARDED RIGID POLYURETHANE FOAMS

CROSS-REFERENCE TO RELATED APPLICATIONS

This application is a U.S. national stage application, filed under 35 U.S.C. § 371, of International Application No. PCT/EP2018/084509, which was filed on Dec. 12, 2018, and which claims priority to European Patent Application No. 17207933.7, which was filed on Dec. 18, 2017. The contents of each are incorporated by reference into this specification.

FIELD

The present invention relates to flame-retardant rigid polyurethane foams and rigid polyurethane/polyisocyanurate foams (hereafter also referred to individually or collectively as “rigid PUR/PIR foams”) with triurethane triols (hereafter also referred to as “TUT”), and also to processes for producing same and to the use of triurethane triols in systems for producing rigid PUR/PIR foams and to mixtures containing a triurethane triol and a compound selected from the group consisting of polyether polyol, polyester polyol, polyether carbonate polyol and polyether ester polyol.

BACKGROUND

The preparation of polyether carbonate polyols by catalytic reaction of alkylene oxides (epoxides) and carbon dioxide in the presence of H-functional starter substances (“starters”) has been the subject of intensive study for more than 40 years (e.g. Inoue et al., Copolymerization of Carbon Dioxide and Epoxide with Organometallic Compounds; Die Makromolekulare Chemie [Macromolecular Chemistry] 130, 210-220, 1969). This reaction is shown schematically in the scheme (I), where R is an organic radical such as alkyl, alkylaryl or aryl, which in each case can also contain heteroatoms such as O, S, Si, etc., and where e, f and g are each an integer, and where the polyether carbonate polyol product shown here in scheme (I) should be interpreted merely as meaning that blocks having the structure shown can in principle be present in the polyether carbonate polyol obtained, but with the order, number and length of the blocks and also the OH functionality of the starter being able to vary and not being restricted to the polyether carbonate polyol shown in scheme (I). This reaction (see scheme (I)) is highly advantageous from an environmental standpoint since this reaction is the conversion of a greenhouse gas such as $CO_2$ to a polymer and hence replaces, i.e. saves, a corresponding amount of alkylene oxide. The by-product formed is the cyclic carbonate shown in scheme (I) (by way of example propylene carbonate for R=$CH_3$, also referred to as cPC hereafter, or ethylene carbonate for R=H, also referred to as cEC hereafter).

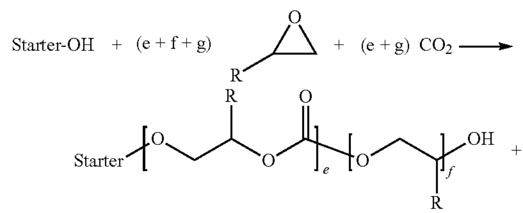

-continued

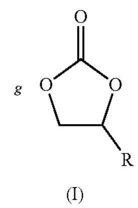

(I)

Double metal cyanide (DMC) catalysts have proven to be particularly advantageous for preparing polyether carbonate polyols of this kind.

EP 3 098 251 A1 discloses a process for preparing diurethane diols from cyclic carbonates and diamines. The diurethane diols obtained are used as H-functional starter compound for preparing polyether polyols. Furthermore, a process for producing flexible polyurethane foams from the polyether polyols obtained is disclosed. However, neither triurethane triols nor the use of diurethane diols as isocyanate-reactive component is disclosed.

SUMMARY

It was therefore an object of the present invention to utilize the cyclic carbonate, obtained as a by-product in the preparation of polyether carbonate polyols, as a material for producing flame-retardant rigid polyurethane foams.

A further object was to improve the flame retardancy of rigid polyurethane foams and reduce the proportion of halogenated flame retardants in the production of rigid polyurethane foams.

According to the invention, this object is achieved by a process for producing rigid PUR/PIR foams containing A1 an isocyanate-reactive component A2 flame retardant A3 blowing agent A4 catalyst A5 optionally auxiliaries and additives B an organic polyisocyanate component characterized in that isocyanate-reactive component A1 contains a triurethane triol A1.1 and a compound A1.2 selected from the group consisting of polyether polyol, polyester polyol, polyether carbonate polyol and polyether ester polyol.

It has surprisingly been found that a mixture containing a triurethane triol A1.1 and a compound A1.2, characterized in that compound A1.2 is selected from the group consisting of polyether polyol, polyester polyol, polyether carbonate polyol and polyether polyol, in a process for producing rigid PUR/PIR foams increases the flame retardancy of the rigid PUR/PIR foams obtained.

DETAILED DESCRIPTION

The use of the word a/an in connection with countable parameters should be understood here and hereinafter to mean the number one only when this is evident from the context (for example through the wording “exactly one”). Otherwise, expressions such as “an alkylene oxide”, “a triurethane triol A1.1” etc. always also comprise those embodiments in which two or more alkylene oxides, two or more triurethane triols A1.1, etc. are used.

The equivalent molar mass is understood to mean the total mass of the material containing active hydrogen atoms divided by the number of active hydrogen atoms. In the case of materials containing hydroxyl groups, it is in the following relationship with the OH number:

$$\text{equivalent molar mass}=56\ 100/\text{OH number [mg KOH/g]}$$

The equivalent molar mass is in the following relationship with the molar mass:

$$\text{molar mass}=\text{equivalent molar mass}*\text{functionality}$$

Functionality refers to the number of active hydrogen atoms per individual molecule. Within the context of the present invention, the terms equivalent molar mass, molar mass and functionality are number-average quantities.

The OH number (also called the hydroxyl number) in the case of a single added polyol indicates the OH number thereof. Data on the OH number for mixtures relate to the number-average OH number of the mixture, calculated from the OH numbers of the individual components in their respective molar proportions. The OH number indicates the amount of potassium hydroxide in milligrams which is equivalent to the amount of acetic acid bound by one gram of substance during acetylation. The OH number is determined within the context of the present invention according to the standard DIN 53240-1 (June 2013).

The invention is illustrated in detail hereinafter. Various embodiments can be combined here with one another as desired, unless the opposite is clearly apparent to the person skilled in the art from the context.

According to the invention, the isocyanate-reactive component A1 contains a triurethane triol A1.1 and a compound A1.2. The triurethane triol A1.1 used according to the invention is obtainable by reaction of cyclic carbonates with compounds containing at least three amino groups, where at least two of the amino groups are primary amino groups. By way of example, the triurethane triols A1.1 are obtainable by reaction of propylene carbonate and/or ethylene carbonate with compounds containing three amino groups, where at least two of the amino groups are primary amino groups.

Preference is given to triurethane triols A1.1 of formula (II)

(II)

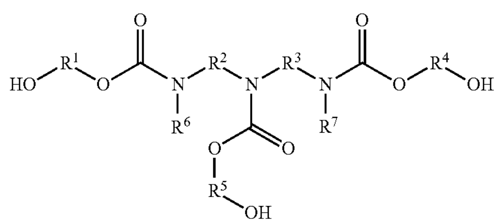

where $R^1$ is linear or branched $C_2$- to $C_{24}$-alkylene which may optionally be interrupted by heteroatoms such as O, S or N and may be substituted, preferably $CH_2—CH_2$ or $CH_2—CH(CH_3)$, $R^2$ is linear or branched $C_2$- to $C_{24}$-alkylene, $C_3$- to $C_{24}$-cycloalkylene, $C_4$- to $C_{24}$-arylene, $C_5$- to $C_{24}$-aralkylene, $C_2$- to $C_{24}$-alkenylene, $C_2$- to $C_{24}$-alkynylene, each of which may optionally be interrupted by heteroatoms such as O, S or N and/or each of which may be substituted by alkyl, aryl and/or hydroxyl, preferably $C_2$- to $C_{24}$-alkylene, $R^3$ is linear or branched $C_2$- to $C_{24}$-alkylene, $C_3$- to $C_{24}$-cycloalkylene, $C_4$- to $C_{24}$-arylene, $C_5$- to $C_{24}$-aralkylene, $C_2$- to $C_{24}$-alkenylene, $C_2$- to $C_{24}$-alkynylene, each of which may optionally be interrupted by heteroatoms such as O, S or N and/or each of which may be substituted by alkyl, aryl and/or hydroxyl, preferably $C_2$- to $C_{24}$-alkylene, $R^4$ is linear or branched $C_2$- to $C_{24}$-alkylene which may optionally be interrupted by heteroatoms such as O, S or N and may be substituted, preferably $CH_2—CH_2$ or $CH_2—CH(CH_3)$, $R^5$ is linear or branched $C_2$- to $C_{24}$-alkylene which may optionally be interrupted by heteroatoms such as O, S or N and may be substituted, preferably $CH_2—CH_2$ or $CH_2—CH(CH_3)$, $R^6$ is H, linear or branched $C_1$- to $C_{24}$-alkyl, $C_3$- to $C_{24}$-cycloalkyl, $C_4$- to $C_{24}$-aryl, $C_5$- to $C_{24}$-aralkyl, $C_2$- to $C_{24}$-alkenyl, $C_2$- to $C_{24}$-alkynyl, each of which may optionally be interrupted by heteroatoms such as O, S or N and/or each of which may be substituted by alkyl, aryl and/or hydroxyl, preferably H, $R^7$ is H, linear or branched $C_1$- to $C_{24}$-alkyl, $C_3$- to $C_{24}$-cycloalkyl, $C_4$- to $C_{24}$-aryl, $C_5$- to $C_{24}$-aralkyl, $C_2$- to $C_{24}$-alkenyl, $C_2$- to $C_{24}$-alkynyl, each of which may optionally be interrupted by heteroatoms such as O, S or N and/or each of which may be substituted by alkyl, aryl and/or hydroxyl, preferably H, and wherein $R^1$ to $R^7$ may be identical or different from one another.

The preferred triurethane triols A1.1 of formula (II) are obtained by reaction of cyclic carbonates with triamines of formula (III)

$$HN(R^6)—R^2—N(R^8)—NH(R^7) \quad \text{(III)}$$

where $R^2$, $R^3$, $R^6$, $R^7$ and $R^8$ are as defined above and where $R^2$, $R^3$, $R^6$, $R^7$ and $R^8$ may be identical or different from one another.

Cyclic carbonates used are preferably propylene carbonate and/or ethylene carbonate.

For example, the triurethane triols A1.1 of formula (II) are obtained by reaction of propylene carbonate and/or ethylene carbonate with triamines of formula (III).

The triurethane triols A1.1 of formula (II) are particularly preferably obtained by reaction of propylene carbonate and/or ethylene carbonate with at least one compound selected from the group consisting of diethylenetriamine, 1,5,10-triazadecane, 1,12-diamino-4,9-diazadodecane, dipropylenetriamine, N-(2-aminoethyl)-1,3-propanediamine and N,N'-bis(3-aminopropyl)-ethylenediamine.

The reaction of the cyclic carbonates with compounds containing at least three amino groups, where at least two of the amino groups are primary amino groups, is preferably effected at 50 to 150° C., particularly preferably at 80 to 120° C. The reaction time is preferably 4 to 40 h, particularly preferably 6 to 30 h. The reaction can take place here in the presence of a catalyst for the aminolysis, such as for example 1,8-diazabicyclo(5.4.0)undec-7-ene.

In a particularly advantageous embodiment, the cyclic carbonate is used at least in an equimolar amount based on cyclic carbonate and amino groups. The molar ratio of cyclic carbonate to the amino groups of the compounds containing at least three amino groups, where at least two of the amino groups are primary amino groups, is preferably 1.0 to 4.0, particularly preferably from 1.4 to 3, very particularly preferably from 2.0 to 2.6.

The excess cyclic carbonate can be removed immediately after the synthesis of the triurethane triol A1.1 by way for example of thin-film evaporation.

However, molar ratios of cyclic carbonate to the amino groups of the compounds containing at least three amino groups, where at least two of the amino groups are primary amino groups, of below 1.00 may also be chosen.

The proportion of triurethane triol A1.1 in the process can be 0.1% to 35.0% by weight, preferably 3.0% to 25.0% by weight, particularly preferably 5.0% to 15.0% by weight, based on the sum total of the masses of components A1.1 and A1.2.

One or more triurethane triols A1.1 can be present in the isocyanate-reactive compound A1.

In addition to the triurethane triol A1.1, at least one compound A1.2 selected from the group consisting of polyether polyols, polyester polyols, polyether ester polyols, polycarbonate polyols and polyether carbonate polyols are used in the process of the invention. Preference is given to polyester polyols and/or polyether polyols and very particular preference is given to polyester polyols. The compound A1.2 can preferably have a hydroxyl number between 100 to 550 mg KOH/g, in particular 100 to 450 mg KOH/g and particularly preferably 100 to 350 mg KOH/g. The individual polyol component preferably has a number-average molecular weight of 120 g/mol to 6000 g/mol, in particular 400 g/mol to 2000 g/mol and particularly preferably 500 g/mol to 1000 g/mol. The OH functionality of the compound A1.2 can be 1.5 to 4.0, preferably 1.8 to 3.0 and particularly preferably 1.9 to 2.5.

The polyester polyols of compound A1.2 may for example be polycondensates of polyhydric alcohols, preferably diols, having 2 to 12 carbon atoms, preferably having 2 to 6 carbon atoms, and polycarboxylic acids, for example di-, tri- or even tetracarboxylic acids, or hydroxycarboxylic acids or lactones; preference is given to using aromatic dicarboxylic acids or mixtures of aromatic and aliphatic dicarboxylic acids. However, it is also possible to use only one or more aliphatic polycarboxylic acids. Instead of the free polycarboxylic acids, it is also possible to use the corresponding polycarboxylic anhydrides or corresponding polycarboxylic esters of lower alcohols to prepare the polyesters, with preference being given to using phthalic anhydride.

Useful carboxylic acids include in particular: succinic acid, glutaric acid, adipic acid, suberic acid, azelaic acid, sebacic acid, decanedicarboxylic acid, tetrahydrophthalic acid, hexahydrophthalic acid, cyclohexanedicarboxylic acid, tetrachlorophthalic acid, itaconic acid, malonic acid, 2-methylsuccinic acid, 3,3-diethylglutaric acid, 2,2-dimethylsuccinic acid, dodecanedioic acid, endomethylenetetrahydrophthalic acid, dimer fatty acid, trimer fatty acid, citric acid, trimellitic acid, benzoic acid, trimellitic acid, maleic acid, fumaric acid, phthalic acid, isophthalic acid and terephthalic acid. Derivatives of these carboxylic acids can also be used, such as for example dimethyl terephthalate. The carboxylic acids can in this case be used either individually or in a mixture. Carboxylic acids used are preferably terephthalic acid, isophthalic acid, adipic acid, sebacic acid, glutaric acid and/or succinic acid; particular preference is given to using adipic acid, glutaric acid and/or succinic acid and mixtures thereof.

Examples of hydroxycarboxylic acids that may be used as co-reactants in the preparation of a polyester polyol having terminal hydroxyl groups include hydroxycaproic acid, hydroxybutyric acid, hydroxydecanoic acid, hydroxystearic acid and the like. Suitable lactones include caprolactone, butyrolactone and homologs.

For preparing the polyester polyols, bio-based starting materials and/or derivatives thereof are in particular also suitable, for example castor oil, polyhydroxy fatty acids, ricinoleic acid, hydroxyl-modified oils, grapeseed oil, black cumin oil, pumpkin seed oil, borage seed oil, soybean oil, wheat germ oil, rapeseed oil, sunflower seed oil, peanut oil, apricot kernel oil, pistachio oil, almond oil, olive oil, macadamia nut oil, avocado oil, sea buckthorn oil, sesame oil, hemp oil, hazelnut oil, primula oil, wild rose oil, safflower oil, walnut oil, fatty acids, hydroxyl-modified and epoxidized fatty acids and fatty acid esters, for example based on myristoleic acid, palmitoleic acid, oleic acid, vaccenic acid, petroselinic acid, gadoleic acid, erucic acid, nervonic acid, linoleic acid, alpha- and gamma-linolenic acid, stearidonic acid, arachidonic acid, timnodonic acid, clupanodonic acid and cervonic acid. Esters of ricinoleic acid with polyfunctional alcohols, for example glycerol, are especially preferred. Preference is also given to the use of mixtures of such bio-based acids with other carboxylic acids, for example phthalic acids.

Examples of suitable diols are ethylene glycol, butylene glycol, diethylene glycol, triethylene glycol, polyalkylene glycols such as polyethylene glycol, and also propane-1,2-diol, propane-1,3-diol, butane-1,3-diol, butane-1,4-diol, hexane-1,6-diol and isomers, neopentyl glycol or neopentyl glycol hydroxypivalate. Preference is given to using ethylene glycol, diethylene glycol, butane-1,4-diol, pentane-1,5-diol, hexane-1,6-diol or mixtures of at least two of the diols mentioned, in particular mixtures of butane-1,4-diol, pentane-1,5-diol and hexane-1,6-diol. Very particular preference is given to using ethylene glycol and diethylene glycol.

In addition, it is also possible to use polyols such as trimethylolpropane, glycerol, erythritol, pentaerythritol, trimethylolbenzene or trishydroxyethyl isocyanurate, with preference being given to glycerol and trimethylolpropane.

In addition, monohydric alkanols can also be used.

Polyether polyols used according to the invention are obtained by preparation methods known to those skilled in the art, such as for example by anionic polymerization of one or more alkylene oxides having 2 to 4 carbon atoms with alkali metal hydroxides, such as sodium or potassium hydroxide, alkali metal alkoxides, such as sodium methoxide, sodium or potassium ethoxide or potassium isopropoxide, or aminic alkoxylation catalysts, such as dimethylethanolamine (DMEOA), imidazole and/or imidazole derivatives, using at least one starter molecule containing 2 to 8, preferably 2 to 6, reactive hydrogen atoms in bonded form.

Examples of suitable alkylene oxides are 1,3-propylene oxide, 1,2- and 2,3-butylene oxide, styrene oxide and preferably ethylene oxide and 1,2-propylene oxide. The alkylene oxides can be used individually, alternately in succession or as mixtures. Preferred alkylene oxides are propylene oxide and ethylene oxide.

Examples of useful starter molecules include: water, organic dicarboxylic acids, such as succinic acid, adipic acid, phthalic acid and terephthalic acid, aliphatic and aromatic, optionally N-mono-, N,N- and N,N'-dialkyl-substituted diamines having 1 to 4 carbon atoms in the alkyl radical, such as optionally mono- and dialkyl-substituted ethylenediamine, diethylenetriamine, triethylenetetramine, 1,3-propylenediamine, 1,3- and 1,4-butylenediamine, 1,2-, 1,3-, 1,4-, 1,5- and 1,6-hexamethylenediamine, phenylenediamines, 2,3-, 2,4- and 2,6-tolylenediamine and 2,2'-, 2,4'- and 4,4'-diaminodiphenylmethane.

Preference is given to using dihydric or polyhydric alcohols such as ethanediol, propane-1,2- and -1,3-diol, diethylene glycol, dipropylene glycol, butane-1,4-diol, hexane- 1,6-diol, triethanolamine, bisphenols, glycerol, trimethylolpropane, pentaerythritol, sorbitol and sucrose.

Polycarbonate polyols that may be used are polycarbonates having hydroxyl groups, for example polycarbonate diols. These are formed in the reaction of carbonic acid derivatives, such as diphenyl carbonate, dimethyl carbonate or phosgene, with polyols, preferably diols.

Examples of such diols are ethylene glycol, propane-1,2- and -1,3-diol, butane-1,3- and -1,4-diol, hexane-1,6-diol, octane-1,8-diol, neopentyl glycol, 1,4-bishydroxymethylcyclohexane, 2-methylpropane-1,3-diol, 2,2,4-trimethylpentane-1,3-diol, dipropylene glycol, polypropylene glycols, dibutylene glycol, polybutylene glycols, bisphenols and lactone-modified diols of the abovementioned type.

Instead of or in addition to pure polycarbonate diols, it is also possible to use polyether polycarbonate diols obtainable for example by copolymerization of alkylene oxides, such as for example propylene oxide, with $CO_2$.

Usable polyether ester polyols are compounds containing ether groups, ester groups and OH groups. Organic dicarboxylic acids having up to 12 carbon atoms are suitable for preparing the polyether ester polyols, preferably aliphatic dicarboxylic acids having 4 to 6 carbon atoms or aromatic dicarboxylic acids used individually or in a mixture. Examples include suberic acid, azelaic acid, decanedicarboxylic acid, maleic acid, malonic acid, phthalic acid, pimelic acid and sebacic acid and in particular glutaric acid, fumaric acid, succinic acid, adipic acid, phthalic acid, terephthalic acid and isophthalic acid. In addition to organic dicarboxylic acids, derivatives of these acids can also be used, for example their anhydrides and also their esters and monoesters with low molecular weight monofunctional alcohols having 1 to 4 carbon atoms. The use of proportions of the abovementioned bio-based starting materials, in particular of fatty acids/fatty acid derivatives (oleic acid, soybean oil etc.), is likewise possible and can have advantages, for example in respect of storage stability of the polyol formulation, dimensional stability, fire behavior and compressive strength of the foams.

Polyether polyols obtained by alkoxylation of starter molecules such as polyhydric alcohols are a further component used for preparing polyether ester polyols. The starter molecules are at least difunctional, but may optionally also contain proportions of higher-functionality, in particular trifunctional, starter molecules.

Examples of starter molecules are diols such as ethane-1,2-diol, propane-1,3-diol, propane-1,2-diol, butane-1,4-diol, pentene-1,5-diol, pentane-1,5-diol, neopentyl glycol, hexane-1,6-diol, heptane-1,7-diol, octane-1,8-diol, decane-1,10-diol, 2-methylpropane-1,3-diol, 2,2-dimethylpropane-1,3-diol, 3-methylpentane-1,5-diol, 2-butyl-2-ethylpropane-1,3-diol, 2-butene-1,4-diol and 2-butyne-1,4-diol, ether diols such as diethylene glycol, triethylene glycol, tetraethylene glycol, dibutylene glycol, tributylene glycol, tetrabutylene glycol, dihexylene glycol, trihexylene glycol, tetrahexylene glycol and oligomer mixtures of alkylene glycols, such as diethylene glycol. Starter molecules having functionalities other than OH can also be used alone or in a mixture.

In addition to the diols, starter molecules also used for preparing the polyethers may also be compounds having more than 2 Zerewitinoff-active hydrogens, in particular having number-average functionalities of 3 to 8, in particular of 3 to 6, for example 1,1,1-trimethylolpropane, triethanolamine, glycerol, sorbitan and pentaerythritol and also triol- or tetraol-started polyethylene oxide polyols.

Polyether ester polyols may also be prepared by the alkoxylation, in particular by ethoxylation and/or propoxylation, of reaction products obtained by the reaction of organic dicarboxylic acids and their derivatives and components with Zerewitinoff-active hydrogens, in particular diols and polyols. Derivatives of these acids that may be used include, for example, their anhydrides, for example phthalic anhydride.

Processes for preparing the polyols have been described for example by Ionescu in “Chemistry and Technology of Polyols for Polyurethanes”, Rapra Technology Limited, Shawbury 2005, p. 55 ff. (chapt. 4: Oligo-Polyols for Elastic Polyurethanes), p. 263 ff. (chapt. 8: Polyester Polyols for Elastic Polyurethanes) and in particular on p. 321 ff. (chapt. 13: Polyether Polyols for Rigid Polyurethane Foams) and p. 419 ff. (chapt. 16: Polyester Polyols for Rigid Polyurethane Foams). It is also possible to obtain polyester and polyether polyols by glycolysis of suitable polymer recyclates. Suitable polyether polycarbonate polyols and the preparation thereof are described, for example, in EP 2 910 585 A1, [0024]-[0041]. Examples of polycarbonate polyols and the preparation thereof can be found, inter alia, in EP 1 359 177 A1. The preparation of suitable polyether ester polyols has been described, inter alia, in WO 2010/043624 A and in EP 1 923 417 A.

The compound A1.2 may contain one or more of the abovementioned compounds.

The isocyanate-reactive component A1 may also contain low molecular weight isocyanate-reactive compounds A1.3; it is in particular possible to use di- or trifunctional amines and alcohols, particularly preferably diols and/or triols having molar masses $M_n$ of less than 400 g/mol, preferably of 60 to 300 g/mol, for example triethanolamine, diethylene glycol, ethylene glycol and glycerol. Where low molecular weight isocyanate-reactive compounds such as these are used for the production of the rigid polyurethane foams, for example in the function as chain extenders and/or crosslinking agents, these are expediently used in an amount of up to 5% by weight, based on the total weight of the isocyanate-reactive component A1.

In addition to the above-described polyols and isocyanate-reactive compounds, the isocyanate-reactive component A1 may contain further isocyanate-reactive compounds A1.4, for example graft polyols, polyamines, polyamino alcohols and polythiols. Of course, the isocyanate-reactive components described also comprise those compounds having mixed functionalities.

The isocyanate-reactive component A1 may contain one or more of the abovementioned compounds. In a preferred embodiment, the isocyanate-reactive component A1 contains only triurethane triol A1.1 and compound A1.2.

The flame retardant A2 used can be compounds such as for example phosphates or phosphonates, for example diethyl ethylphosphonate (DEEP), triethyl phosphate (TEP), triphenyl phosphate (TPP), tricresyl phosphate, diphenyl cresyl phosphate (DPC), dimethyl methylphosphonate (DMMP), diethyl diethanolaminomethylphosphonate, 9,10-dihydro-9-oxa-10-phosphorylphenanthrene-10-oxide (DOPO) and dimethyl propylphosphonate (DMPP). Examples of further suitable flame retardants A2 are brominated esters, brominated ethers (Ixol) or brominated alcohols such as dibromoneopentyl alcohol, tribromoneopentyl alcohol, tetrabromophthalate diol, and also chlorinated phosphates such as tris(2-chloroethyl) phosphate, tris(2-chloropropyl) phosphate (TCPP), tris(1,3-dichloropropyl) phosphate, tris(2,3-dibromopropyl) phosphate, tetrakis(2-chloroethyl) ethylenediphosphate and also commercially available halogen-containing flame-retardant polyols. The proportion of flame retardant A2 can be 2.0% by weight to 30.0% by weight, preferably 4.0% by weight to 25.0% by weight, particularly preferably 8.0% by weight to 20.0% by weight, based on the sum total of the masses of components A1 to A5.

The blowing agent A3 used can be a physical blowing agent, such as for example low-boiling organic compounds such as, for example, hydrocarbons, halogenated hydrocarbons, ethers, ketones, carboxylic esters or carbonic esters. Organic compounds inert towards the isocyanate component B and having boiling points below 100° C., preferably below 50° C., at atmospheric pressure are suitable in particular. These boiling points have the advantage that the organic compounds evaporate under the influence of the exothermic polyaddition reaction. Examples of such preferably used organic compounds are alkanes, such as heptane, hexane, n-pentane and isopentane, preferably technical grade mixtures of n-pentane and isopentane, n-butane and isobutane and propane, cycloalkanes, such as cyclopentane and/or cyclohexane, ethers, such as furan, dimethyl ether and diethyl ether, ketones, such as acetone and methyl ethyl ketone, alkyl carboxylates, such as methyl formate, dimethyl oxalate and ethyl acetate and halogenated hydrocarbons, such as methylene chloride, dichloromonofluoromethane, difluoromethane, trifluoromethane, difluoroethane, tetrafluoroethane, chlorodifluoroethanes, 1,1-dichloro-2,2,2-trifluoroethane, 2,2-dichloro-2-fluoroethane and heptafluoropropane. Also preferred is the use of (hydro)fluorinated olefins, for example HFO 1233zd(E) (trans-1-chloro-3,3,3-trifluoro-1-propene) or HFO 1336mzz(Z) (cis-1,1,1,4,4,4-hexafluoro-2-butene) or additives such as FA 188 from 3M (1,1,1,2,3,4,5,5,5-nonafluoro-4-(trifluoromethyl)pent-2-ene). It is also possible to use mixtures of two or more of the organic compounds mentioned. The organic compounds may also be used here in the form of an emulsion of small droplets.

The blowing agent A3 used can also be a chemical blowing agent, such as for example water, carboxylic acid and mixtures thereof. These react with isocyanate groups to form the blowing gas, forming carbon dioxide for example in the case of water and forming carbon dioxide and carbon monoxide in the case of for example formic acid. The carboxylic acid used is preferably at least one compound selected from the group consisting of formic acid, acetic acid, oxalic acid and ricinoleic acid. The chemical blowing agent used is particularly preferably water.

Halogenated hydrocarbons are preferably not used as blowing agent.

The blowing agent A3 used is at least one compound selected from the group consisting of physical and chemical blowing agents. Preference is given to using only physical blowing agent.

Catalysts A4 used for producing the rigid PUR/PIR foams are compounds which accelerate the reaction of the compounds containing reactive hydrogen atoms, in particular hydroxyl groups, with the isocyanate component B, such as for example tertiary amines or metal salts. The catalyst components may be metered into the reaction mixture or else be fully or partially initially charged in the isocyanate-reactive component A1.

By way of example, tertiary amines are used, such as triethylamine, tributylamine, dimethylbenzylamine, dicyclohexylmethylamine, dimethylcyclohexylamine, N,N,N',N'-tetramethyldiaminodiethyl ether, bis(dimethylaminopropyl)urea, N-methyl- or N-ethylmorpholine, N-cyclohexylmorpholine, N,N,N',N'-tetramethylethylenediamine, N,N,N,N-tetramethylbutanediamine, N,N,N,N-tetramethylhexane-1,6-diamine, pentamethyldiethylenetriamine, bis[2-(dimethylamino)ethyl] ether, dimethylpiperazine, N-dimethylaminoethylpiperidine, 1,2-dimethylimidazole, 1-azabicyclo[3,3,0]octane, 1,4-diazabicyclo[2,2,2]octane (Dabco) and alkanolamine compounds such as triethanolamine, triisopropanolamine, N-methyl- and N-ethyldiethanolamine, dimethylaminoethanol, 2-(N,N-dimethylaminoethoxy)ethanol, N,N',N"-tris(dialkylaminoalkyl)hexahydrotriazine, for example N,N',N"-tris(dimethylaminopropyl)hexahydrotriazine and triethylenediamine.

Metal salts, such as for example alkali metal or transition metal salts, may also be used. Transition metal salts used are for example zinc salts, bismuth salts, iron salts, lead salts or preferably tin salts. Examples of transition metal salts used are iron(II) chloride, zinc chloride, lead octoate, tin dioctoate, tin diethylhexoate and dibutyltin dilaurate. The transition metal salt is particularly preferably selected from at least one compound from the group consisting of tin dioctoate, tin diethylhexoate and dibutyltin dilaurate. Examples of alkali metal salts are alkali metal alkoxides such as for example sodium methoxide and potassium isopropoxide, alkali metal carboxylates such as for example potassium acetate, and also alkali metal salts of long-chain fatty acids having 10 to 20 carbon atoms and optionally pendant OH groups. The alkali metal salt used is preferably one or more alkali metal carboxylates.

Useful catalysts A4 furthermore include: amidines such as for example 2,3-dimethyl-3,4,5,6-tetrahydropyrimidine, tetraalkylammonium hydroxides such as for example tetramethylammonium hydroxide, alkali metal hydroxides such as for example sodium hydroxide, and tetraalkylammonium carboxylates or phosphonium carboxylates. Mannich bases and salts of phenols are also suitable catalysts.

If a relatively large polyisocyanate excess is used when foaming, useful catalysts for the trimerization reaction of the excess NCO groups with one another furthermore include: catalysts forming isocyanurate groups, for example ammonium ion salts or alkali metal salts, especially ammonium carboxylates or alkali metal carboxylates, alone or in combination with tertiary amines. The isocyanurate formation results in particularly flame-retardant PIR foams.

The abovementioned catalysts may be used alone or in combination with one another.

One or more auxiliaries and additives may optionally be used as component A5. Examples of component A5 are surface-active substances, cell regulators, fillers, dyes, pigments, hydrolysis stabilizers, fungistatic and bacteriostatic substances.

Useful surface-active substances include for example compounds that serve to promote the homogenization of the starting substances and are optionally also suitable for regulating the cell structure of the plastics. Examples include emulsifiers, such as the sodium salts of castor oil sulfates or of fatty acids and salts of fatty acids with amines, for example diethylamine oleate, diethanolamine stearate, diethanolamine ricinoleate, salts of sulfonic acids, for example alkali metal or ammonium salts of dodecylbenzenedisulfonic acid or dinaphthylmethanedisulfonic acid and ricinoleic acid; foam stabilizers, such as siloxane oxyalkylene mixed polymers and other organopolysiloxanes, ethoxylated alkylphenols, ethoxylated fatty alcohols, paraffin oils, castor oil esters or ricinoleic esters, Turkey red oil and peanut oil, and cell regulators, such as paraffins, fatty alcohols and dimethylpolysiloxanes.

Suitable fillers, in particular reinforcing fillers, are the customary organic and inorganic fillers, reinforcers, weighting agents, agents for improving abrasion characteristics in paints, coating agents etc. which are known per se. These especially include for example: inorganic fillers such as siliceous minerals, for example phyllosilicates such as antigorite, serpentine, hornblendes, amphiboles, chrysotile, montmorillonite and talc, metal oxides such as kaolin, aluminum oxides, titanium oxides and iron oxides, metal salts, such as chalk, barite and inorganic pigments such as cadmium sulfide and zinc sulfide and also glass inter alia, and natural and synthetic fibrous minerals such as wollastonite, metal fibers and in particular glass fibers of various lengths which may optionally have been coated with a size. Examples of useful organic fillers include: carbon, melamine, colophony, cyclopentadienyl resins and graft polymers and also cellulose fibers, polyamide fibers, polyacrylonitrile fibers, polyurethane fibers and polyester fibers based on aromatic and/or aliphatic dicarboxylic esters and carbon fibers.

Suitable organic polyisocyanate components B are aliphatic, cycloaliphatic, araliphatic, aromatic and heterocyclic polyisocyanates, such as are described for example by W. Siefken in Justus Liebigs Annalen der Chemie, 562, pages 75 to 136, for example those of formula (IV)

$$Q(NCO)_n, \quad (IV)$$

in which n=2-4, preferably 2-3, and

Q is an aliphatic hydrocarbon radical having 2-18, preferably 6-10, carbon atoms, a cycloaliphatic hydrocarbon radical having 4-15, preferably 6-13, carbon atoms or an araliphatic hydrocarbon radical having 8-15, preferably 8-13, carbon atoms.

For example, the polyisocyanates are those as described in EP 0 007 502 A1, pages 7-8. Preference is generally given to the readily industrially available polyisocyanates, for example tolylene 2,4- and 2,6-diisocyanate and any desired mixtures of these isomers ("TDI"); polyphenylpolymethylene polyisocyanates as prepared by aniline-formaldehyde condensation and subsequent phosgenation ("crude MDI"), and polyisocyanates having carbodiimide groups, urethane groups, allophanate groups, isocyanurate groups, urea groups or biuret groups ("modified polyisocyanates"), especially those modified polyisocyanates which derive from tolylene 2,4- and/or 2,6-diisocyanate or from diphenylmethane 4,4'- and/or 2,4'-diisocyanate. The polyisocyanates containing urethane groups (prepolymers) may, for example, be reaction products of the polyisocyanates with polyester polyols or else any other polyols (for example conventional polyether polyols). The polyisocyanate used is preferably at least one compound selected from the group consisting of tolylene 2,4- and 2,6-diisocyanate, diphenylmethane 4,4'- and 2,4'- and 2,2'-diisocyanate and polyphenylpolymethylene polyisocyanate ("polycyclic MDI"); the polyisocyanate used is particularly preferably a mixture comprising diphenylmethane 4,4'-diisocyanate and diphenylmethane 2,4'-diisocyanate and polyphenylpolymethylene polyisocyanate.

It is possible that in the reaction mixture the number of NCO groups in the isocyanate and the number of isocyanate-reactive groups result in an index of 90 to 600, preferably between 115 and 400. This index is preferably in a range from 150 to 450 in which a higher proportion of polyisocyanurates (PIR) is present (the rigid foam is referred to as a rigid PIR foam or rigid PUR/PIR foam) and results in a higher flame retardancy of the rigid PUR/PIR foam itself. Another preferred range for the isocyanate index is the range of values from 90 to 150 (the rigid foam is referred to as a rigid polyurethane foam (rigid PUR foam)), with for example a reduced brittleness compared to rigid PUR/PIR foam.

The isocyanate index (also called index) is to be understood as meaning the quotient of the molar amount [mol] of isocyanate groups actually used and the molar amount [mol] of isocyanate-reactive groups actually used, multiplied by 100:

$$\text{index}=(\text{moles of isocyanate groups}/\text{moles of isocyanate-reactive groups})*100$$

The NCO value (also called NCO content, isocyanate content) is determined as per EN ISO 11909 (May 2007).

The invention likewise relates to a rigid PUR/PIR foam which has been produced by the process according to the invention.

The rigid PUR/PIR foams according to the invention are preferably produced by one-step processes known to those skilled in the art and in which the reaction components are continuously or discontinuously reacted with one another and then subsequently introduced either manually or with the aid of mechanical equipment in the high-pressure or low-pressure process after discharge onto a conveyor belt or into suitable molds for curing. Examples are described in U.S. Pat. No. 2,764,565, in G. Oertel (ed.) "Kunststoff-Handbuch" [Plastics Handbook], Volume VII, Carl Hanser Verlag, 3rd edition, Munich 1993, pages 267 ff., and in K. Uhlig (ed.) "Polyurethan Taschenbuch" [Polyurethane Handbook], Carl Hanser Verlag, 2nd edition, Vienna 2001, pages 83-102. The rigid PUR/PIR foams may have an apparent density of 25.0 to 300.0 kg/$m^3$, preferably 25.0 to 80.0 kg/$m^3$, particularly preferably 30.0 to 65.0 kg/$m^3$ and especially 30.0 to 45.0 kg/$m^3$.

The rigid PUR/PIR foams of the invention are preferably used for the production of composite elements. The foaming typically takes place here continuously or discontinuously against at least one outer layer.

The invention accordingly further provides for the use of a rigid PUR/PIR foam according to the invention as an insulation foam and/or as an adhesion promoter in composite elements, wherein the composite elements comprise a layer, comprising a rigid PUR/PIR foam according to the invention, and at least one outer layer. In this case, the outer layer is at least partially contacted by a layer comprising the rigid PUR/PIR foam according to the invention.

Composite elements of the type of interest here are also known as sandwich elements or insulation panels and are generally used as components for soundproofing, thermal insulation, for commercial buildings or for façade construction. The one or two outer layers may in each case be a flexible outer layer, for example an aluminum foil, paper, plastics webs, multilayer outer layers made from paper and aluminum or from mineral nonwovens, and/or a rigid outer layer, for example made from steel sheet or up to 7 mm-thick particleboards, depending on the purpose of use of the composite elements.

In a first embodiment, the invention therefore relates to a process for producing rigid PUR/PIR foams containing A1 an isocyanate-reactive component A2 flame retardant A3 blowing agent A4 catalyst A5 optionally auxiliaries and additives B an organic polyisocyanate component characterized in that component A1 contains a triurethane triol A1.1 and a compound A1.2 selected from the group consisting of polyether polyol, polyester polyol, polyether carbonate polyol and polyether ester polyol.

In a second embodiment, the invention relates to a process as per the first embodiment, characterized in that the isocyanate-reactive component A1 contains a compound A1.2 having a hydroxyl number of 100 to 550 mg KOH/g, preferably 100 to 450 mg KOH/g, particularly preferably 100 to 350 mg KOH/g.

In a third embodiment, the invention relates to a process as per either of embodiments 1 and 2, characterized in that the isocyanate-reactive component A1 contains a compound A1.2 having an OH functionality of 1.5 to 4.0, preferably 1.8 to 3.0, particularly preferably 1.9 to 2.5.

In a fourth embodiment, the invention relates to a process as per any of embodiments 1 to 3, characterized in that compound A1.2 is a polyester polyol or a polyether polyol, preferably a polyester polyol.

In a fifth embodiment, the invention relates to a process as per any of embodiments 1 to 4, characterized in that compound A1.2 is a polyester polyol obtainable from the reaction of aliphatic and/or aromatic dicarboxylic acid with at least one aliphatic diol.

In a sixth embodiment, the invention relates to a process as per any of embodiments 1 to 5, characterized in that the triurethane triol A1.1 has a structure of formula (II)

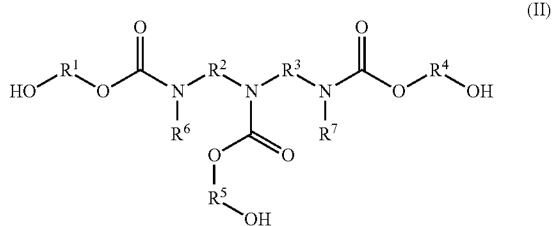

(II)

where $R^1$ is linear or branched $C_2$- to $C_{24}$-alkylene which may optionally be interrupted by heteroatoms such as O, S or N and may be substituted, preferably $CH_2—CH_2$ or $CH_2—CH(CH_3)$, $R^2$ is linear or branched $C_2$- to $C_{24}$-alkylene, $C_3$- to $C_{24}$-cycloalkylene, $C_4$- to $C_{24}$-arylene, $C_5$- to $C_{24}$-aralkylene, $C_2$- to $C_{24}$-alkenylene, $C_2$- to $C_{24}$-alkynylene, each of which may optionally be interrupted by heteroatoms such as O, S or N and/or each of which may be substituted by alkyl, aryl and/or hydroxyl, preferably $C_2$- to $C_{24}$-alkylene, $R^3$ is linear or branched $C_2$- to $C_{24}$-alkylene, $C_3$- to $C_{24}$-cycloalkylene, $C_4$- to $C_{24}$-arylene, $C_5$- to $C_{24}$-aralkylene, $C_2$- to $C_{24}$-alkenylene, $C_2$- to $C_{24}$-alkynylene, each of which may optionally be interrupted by heteroatoms such as O, S or N and/or each of which may be substituted by alkyl, aryl and/or hydroxyl, preferably $C_2$- to $C_{24}$-alkylene, $R^4$ is linear or branched $C_2$- to $C_{24}$-alkylene which may optionally be interrupted by heteroatoms such as O, S or N and may be substituted, preferably $CH_2—CH_2$ or $CH_2—CH(CH_3)$, $R^5$ is linear or branched $C_2$- to $C_{24}$-alkylene which may optionally be interrupted by heteroatoms such as O, S or N and may be substituted, preferably $CH_2—CH_2$ or $CH_2—CH(CH_3)$, $R^6$ is H, linear or branched $C_1$- to $C_{24}$-alkyl, $C_3$- to $C_{24}$-cycloalkyl, $C_4$- to $C_{24}$-aryl, $C_5$- to $C_{24}$-aralkyl, $C_2$- to $C_{24}$-alkenyl, $C_2$- to $C_{24}$-alkynyl, each of which may optionally be interrupted by heteroatoms such as O, S or N and/or each of which may be substituted by alkyl, aryl and/or hydroxyl, preferably H, $R^7$ is H, linear or branched $C_1$- to $C_{24}$-alkyl, $C_3$- to $C_{24}$-cycloalkyl, $C_4$- to $C_{24}$-aryl, $C_5$- to $C_{24}$-aralkyl, $C_2$- to $C_{24}$-alkenyl, $C_2$- to $C_{24}$-alkynyl, each of which may optionally be interrupted by heteroatoms such as O, S or N and/or each of which may be substituted by alkyl, aryl and/or hydroxyl, preferably H, and wherein $R^1$ to $R^7$ may be identical or different from one another.

In a seventh embodiment, the invention relates to a process as per any of embodiments 1 to 6, characterized in that the triurethane triol A1.1 is obtained from the reaction between cyclic ethylene carbonate and/or cyclic propylene carbonate with a compound containing at least three amino groups, where at least two of the amino groups are primary amino groups.

In an eighth embodiment, the invention relates to a process as per any of embodiments 1 to 7, characterized in that the proportion of triurethane triol A1.1 is 0.1% to 35.0% by weight, preferably 3.0% to 25.0% by weight, particularly preferably 5.0% to 15.0% by weight, based on the sum total of the masses of components A1.1 and A1.2.

In a ninth embodiment, the invention relates to a process as per any of embodiments 1 to 8, characterized in that the isocyanate index is 100 to 500, preferably 180 to 450.

In a tenth embodiment, the invention relates to a process as per any of embodiments 1 to 9, characterized in that flame retardant A2 in a proportion of 2.0% by weight to 30.0% by weight, preferably 4.0% by weight to 25.0% by weight, particularly preferably 8.0% by weight to 20.0% by weight, based on the weight of components A1 to A5.

In an eleventh embodiment, the invention relates to a process as per any of embodiments 1 to 10, characterized in that the polyisocyanate component B used is at least one compound selected from the group consisting of tolylene 2,4- and 2,6-diisocyanate, diphenylmethane 4,4'- and 2,4'- and 2,2'-diisocyanate and polyphenylpolymethylene polyisocyanate ("polycyclic MDI").

In a twelfth embodiment, the invention relates to a rigid PUR/PIR foam obtainable by a process as per any of embodiments 1 to 11.

In a thirteenth embodiment, the invention relates to a rigid PUR/PIR foam as per the twelfth embodiment, characterized in that the apparent density is 25.0 to 300.0 $kg/m^3$, preferably 25.0 to 80.0 $kg/m^3$, particularly preferably 30.0 to 65.0 $kg/m^3$ and especially 30.0 to 45.0 $kg/m^3$.

In a fourteenth embodiment, the invention relates to the use of a rigid PUR/PIR foam as per either of embodiments 13 and 14 as an insulating material or composite element with flexible or non-flexible outer layers.

In a fifteenth embodiment, the invention relates to a mixture containing a triurethane triol A1.1 and a component A1.2, characterized in that the component A1.2 is selected from the group consisting of polyether polyol, polyester polyol, polyether carbonate polyol and polyether ester polyol.

In a sixteenth embodiment, the invention relates to a process as per any of embodiments 1 to 10, characterized in that the triurethane triol A1.1 is obtained by reaction of cyclic carbonates with triamines of formula (III), $$HN(R^6)—R^2—N(R^8)—NH(R^7) \quad (III)$$

where $R^2$, $R^3$, $R^6$, $R^7$ and $R^8$ are as defined above and where $R^2$, $R^3$, $R^6$, $R^7$ and $R^8$ may be identical or different from one another.

In a seventeenth embodiment, the invention relates to a process as per any of embodiments 1 to 10, characterized in that the triurethane triol A1.1 is obtained from the reaction between cyclic propylene carbonate and/or cyclic ethylene carbonate with at least one compound selected from the group consisting of diethylenetriamine, 1,5,10-triazadecane, 1,12-diamino-4,9-diazadodecane, dipropylenetriamine, N-(2-aminoethyl)-1,3-propanediamine and N,N'-bis(3-aminopropyl)ethylenediamine.

The preferred embodiments may be performed individually or else in conjunction with one another.

EXAMPLES

Test methods:

Hydroxyl number: The OH number was determined according to the method of DIN 53240-1 (method without catalyst, June 2013 version).

Amine number: Total base number according to DIN 51639-1, in the November 2014 version.

Acid number: The acid number was determined according to DIN EN ISO 2114 (June 2002).

Fiber time: The fiber time ("gel point $t_G$") is determined by dipping a wooden rod into the reacting polymer melt and withdrawing it again. It characterizes the time from which the polymer melt hardens. The time stated as to is the time at which threads can for the first time be drawn between the wooden rod and the polymer melt.

Cream time: The period of time that elapses from the start of mixing the main components up to the visible commencement of foaming of the mixture.

Viscosity: The dynamic viscosity was measured using the MCR 51 rheometer from Anton Paar in accordance with DIN 53019-1 (September 2008 version) with a CP 50-1 measuring cone (50 mm diameter, 1° angle) at shear rates of 25 $s^{-1}$, 100 $s^{-1}$, 200 $s^{-1}$ and 500 $s^{-1}$. The polyols according to the invention and not according to the invention display viscosity values that are independent of the shear rate.

Apparent density: The apparent density was ascertained according to DIN EN ISO 845 (October 2009 version).

Fire properties: The fire properties were determined according to DIN 4102-1 (May 1998 version).

Compressive strength: The compressive strength of the rigid PUR/PIR foams was determined according to DIN EN ISO 844 (November 2014 version).

Open-cell content: The open-cell content of the rigid PUR/PIR foams was ascertained according to DIN EN ISO 4590 (June 2014 version).

Raw Materials Used:

cPC: cyclic propylene carbonate (Acros)

DBU: 1,8-diazabicyclo(5.4.0)undec-7-ene

DETA: diethylenetriamine

A1.2-1: aliphatic polyester polyol formed from technical grade glutaric acid (mixture of glutaric acid, succinic acid and adipic acid, Lanxess AG) and ethylene glycol, hydroxyl number: 237 mg KOH/g, acid number: 1.9 mg KOH/g, viscosity: 1160 mPas at 25° C.

A1.2-2: linear polyester polyol, hydroxyl number: 240 mg KOH/g (Desmophen®2382, Covestro Deutschland GmbH)

A1.2-3: containing the reaction product of phthalic anhydride and diethylene glycol, acid number: 97 mg KOH/g (Additive 1132, Covestro Deutschland AG)

A1.2-4: amine-based polyether polyol, hydroxyl number: 395 to 435 mg KOH/g, viscosity: 6450-9550 mPas at 25° C. (Desmophen®T 460, Covestro Deutschland GmbH)

A2-1: trischloroisopropyl phosphate (Levagard®PP, Lanxess AG)

A2-2: triethyl phosphate (Levagard®TEP-Z, Lanxess AG)

A3-1: n-pentane (Kraemer&Martin GmbH)

A4-1: activator for the production of rigid polyurethane foams (Desmorapid®DB, Covestro Deutschland AG)

A4-2: potassium acetate in diethylene glycol (Desmorapid®PU 1792, Covestro Deutschland AG)

A5-1: modified polyethersiloxane (Tegostab®B 8443, Evonik)

B-1: polyisocyanate having an NCO content of 30.5% to 32.5% by weight (Desmodur®44V20 L, Covestro Deutschland AG)

Preparation of Triurethane Triol A1.1-1:

A 500 ml flange reactor with heatable jacket and electric stirrer is initially charged with 348.7 g (3.42 mol) of cPC and 2.22 g (14.6 mmol) of DBU under inert gas ($N_2$). Thereafter, 50.3 g (0.49 mol) of DETA is added dropwise over the course of one hour while stirring and at 100° C. Subsequently, the reaction was stirred further for a total of 6 h at 100° C.

Excess cPC was removed by short-path evaporation at a pressure of 0.01 mbar, with the jacket temperature being 140° C. and a metering rate of 200 g/hour being selected.

Analysis:

Viscosity: 95 500 mPas (50° C.), 3900 mPas (75° C.)

Hydroxyl number: 366 mg KOH/g

Amine number: 43.3 mg KOH/g

Preparation of a Mixture Containing a Triurethane Triol A1.1 and a Compound A1.2:

10 g of the triurethane triol A1.1-2 are preheated to 100° C. in a drying cabinet and added to 90 g of A1.2-1 preheated to 60° C. The mixture is stirred by means of a Pendraulik stirrer until homogeneous and has a hydroxyl number of 250 mg KOH/g.

Production of the Rigid PUR/PIR Foams:

To produce the rigid PUR/PIR foams, the isocyanate-reactive components, flame retardants, catalysts, blowing agents and foam stabilizer are mixed, polyisocyanate is added to the mixture obtained and the mixture is poured into a paper mold (30×30×10 $cm^3$) and reacted to completion therein. The formulations and results of the physical measurements on the samples obtained are shown in table 1.

TABLE 1

Production of rigid PUR/PIR foams using A1.1-1

| | | Example | | | |
|---|---|---|---|---|---|
| | | 1 (comp.) | 2 | 3 | 4 |
| A1.2-2 | [g] | 74.9 | | | |
| Mixture containing TUT A1.1-1 and polyester polyol A1.2-1 | [g] | | 76.4 | 79.2 | 80.7 |
| A1.2-3 | [g] | 2.59 | 2.64 | 2.74 | 2.79 |
| A1.2-4 | [g] | 5.86 | 5.97 | 6.19 | 6.31 |
| A2-1 | [g] | 23.4 | 23.9 | 12.4 | 6.3 |
| A2-2 | [g] | 5.86 | 5.97 | 6.19 | 6.31 |
| A3-1 | [g] | 16.13 | 15.92 | 15.82 | 15.77 |
| A4-1 | [g] | 1.69 | 2.87 | 2.98 | 3.03 |
| A4-2 | [g] | 4.17 | 3.22 | 3.34 | 3.4 |
| A5-1 | [g] | 3.94 | 4.02 | 4.17 | 4.25 |

TABLE 1-continued

Production of rigid PUR/PIR foams using A1.1-1

| | | Example | | | |
|---|---|---|---|---|---|
| | | 1 (comp.) | 2 | 3 | 4 |
| B-1 | [g] | 211.4 | 209.1 | 217 | 221.1 |
| Isocyanate index | | 325.1 | 325.1 | 325.1 | 325.1 |
| Analysis | | | | | |
| Processing: | | | | | |
| Cream time | [s] | 15 | 17 | 17 | 18 |
| Gel time | [s] | 43 | 47 | 46 | 46 |
| Tack-free time | [s] | 63 | 65 | 61 | 66 |
| Properties: | | | | | |
| Apparent density, core | [kg/m$^3$] | 42.3 | 41.6 | 41.4 | 41.2 |
| Compressive strength, transverse | [kPa] | 225 | 202 | 205 | 209 |
| Compressive strength, parallel | [kPa] | 375 | 318 | 336 | 342 |
| Open-cell content | [%] | 5.2 | 5.7 | 5.7 | 5.1 |
| Flame height | [mm] | 140-145 | 125-130 | 135-140 | 130-140 |
| Classification | | B2 | B2 | B2 | B2 |

Table 1 shows in examples 2 to 4 that the use of the mixture according to the invention leads to rigid PUR/PIR foams having a B2 fire classification. Compared with comparative example 1, the rigid PUR/PIR foams of the process according to the invention (examples 2 to 4 according to the invention) possess improved flame retardancy (see table 1: analysis). Examples 3 and 4 according to the invention show that the proportion of flame retardant in the rigid PUR/PIR foams, in particular of the halogen-containing flame retardant TCPP, can be reduced. Despite a reduced proportion of flame retardant, the flame retardancy of the rigid PUR/PIR foams is at least equivalent to the flame retardancy of the rigid PUR/PIR foams of comparative example 1.

In addition, table 1 (analysis) proves that all relevant processing-related parameters, such as for example cream time, gel time and tack-free time, remain practically unchanged compared to comparative example 1 if relatively small adjustments of the catalysts and stabilizers are made. Under these prerequisites, all mechanical properties of the rigid PUR/PIR foams of the examples according to the invention also maintain the level given by comparative example 1.

What is claimed is:

1. A process for producing rigid PUR/PIR foams comprising mixing and reacting a composition, the composition comprising:

A1 an isocyanate-reactive component,

A2 a flame retardant,

A3 a blowing agent,

A4 a catalyst,

A5 optionally auxiliaries and additives, and

B an organic polyisocyanate component, wherein component A1 comprises a triurethane triol A1.1 and a compound A1.2 selected from the group consisting of polyether polyol, polyester polyol, polyether carbonate polyol, and polyether ester polyol, wherein the triurethane triol A1.1 has a structure of formula (II)

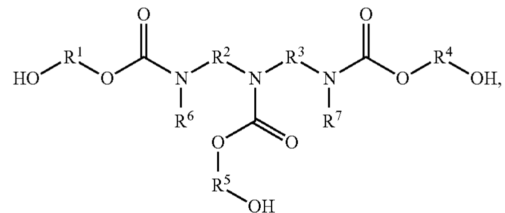

wherein $R^1$ is linear or branched $C_2$- to $C_{24}$-alkylene which may optionally be interrupted by heteroatoms and may optionally be substituted, $R^2$ is linear or branched $C_2$- to $C_{24}$-alkylene, $C_3$- to $C_{24}$-cycloalkylene, $C_4$- to $C_{24}$-arylene, $C_5$- to $C_{24}$-aralkylene, $C_2$- to $C_{24}$-alkenylene, or $C_2$- to $C_{24}$-alkynylene, each of which may optionally be interrupted by heteroatoms and/or each of which may optionally be substituted by alkyl, aryl, and/or hydroxyl, $R^3$ is linear or branched $C_2$- to $C_{24}$-alkylene, $C_3$- to $C_{24}$-cycloalkylene, $C_4$- to $C_{24}$-arylene, $C_5$- to $C_{24}$-aralkylene, $C_2$- to $C_{24}$-alkenylene, or $C_2$- to $C_{24}$-alkynylene, each of which may optionally be interrupted by heteroatoms and/or each of which may optionally be substituted by alkyl, aryl, and/or hydroxyl, $R^4$ is linear or branched $C_2$- to $C_{24}$-alkylene which may optionally be interrupted by heteroatoms and may optionally be substituted, $R^5$ is linear or branched $C_2$- to $C_{24}$-alkylene which may optionally be interrupted by heteroatoms and may optionally be substituted, $R^6$ is H, linear or branched $C_1$- to $C_{24}$-alkyl, $C_3$- to $C_{24}$-cycloalkyl, $C_4$- to $C_{24}$-aryl, $C_5$- to $C_{24}$-aralkyl, $C_2$- to $C_{24}$-alkenyl, or $C_2$- to $C_{24}$-alkynyl, each of which may optionally be interrupted by heteroatoms and/or each of which may optionally be substituted by alkyl, aryl, and/or hydroxyl, $R^7$ is H, linear or branched $C_1$- to $C_{24}$-alkyl, $C_3$- to $C_{24}$-cycloalkyl, $C_4$- to $C_{24}$-aryl, $C_5$- to $C_{24}$-aralkyl, $C_2$- to $C_{24}$-alkenyl, or $C_2$- to $C_{24}$-alkynyl, each of which may optionally be interrupted by heteroatoms and/or each of which may optionally be substituted by alkyl, aryl, and/or hydroxyl, and wherein $R^1$ to $R^7$ may be identical or different from one another.

2. The process as claimed in claim 1, wherein the isocyanate-reactive component A1 comprises the compound A1.2, and the compound A1.2 has a hydroxyl number of 100 to 550 mg KOH/g.

3. The process as claimed in claim 1, wherein the isocyanate-reactive component A1 comprises the compound A1.2, and the compound A1.2 has an OH functionality of 1.5 to 4.0.

4. The process as claimed in claim 1, wherein the compound A1.2 is a polyester polyol or a polyether polyol.

5. The process as claimed in claim 1, wherein the compound A1.2 is a polyester polyol obtainable from the reaction of aliphatic and/or aromatic dicarboxylic acid with at least one aliphatic diol.

6. The process as claimed in claim 1, wherein the triurethane triol A1.1 is obtained from the reaction between cyclic ethylene carbonate and/or cyclic propylene carbonate with a compound containing at least three amino groups, wherein at least two of the amino groups are primary amino groups.

7. The process as claimed in claim 1, wherein the proportion of triurethane triol A1.1 is 0.1% to 35.0% by weight, based on the sum total of the masses of components A1.1 and A1.2.

8. The process as claimed in claim 1, wherein the isocyanate index is 100 to 500.

9. The process as claimed in claim 1, wherein the flame retardant A2 is in a proportion of 2.0% by weight to 30.0% by weight, based on the weight of components A1 to A5.

10. The process as claimed in claim 1, wherein the polyisocyanate component B used is at least one compound selected from the group consisting of tolylene 2,4- and 2,6-diisocyanate, diphenylmethane 4,4'- and 2,4'- and 2,2'-diisocyanate, and polyphenylpolymethylene polyisocyanate ("polycyclic MDI").

* * * * *